United States Patent
Leibold

(10) Patent No.: US 10,813,736 B2
(45) Date of Patent: Oct. 27, 2020

(54) THERAPEUTIC JOINT SUPPORT FOR ANIMALS

(75) Inventor: Mary Braun Leibold, South Russell, OH (US)

(73) Assignee: Mary Braun Leibold, South Russell, OH (US)

( * ) Notice: Subject to any disclaimer, the term of this patent is extended or adjusted under 35 U.S.C. 154(b) by 731 days.

(21) Appl. No.: 13/092,426

(22) Filed: Apr. 22, 2011

(65) Prior Publication Data

US 2011/0288460 A1  Nov. 24, 2011

Related U.S. Application Data

(60) Provisional application No. 61/395,809, filed on May 18, 2010.

(51) Int. Cl.
  *A61F 5/00* (2006.01)
  *A61D 9/00* (2006.01)
(52) U.S. Cl.
  CPC .................................... *A61D 9/00* (2013.01)
(58) Field of Classification Search
  CPC ................ A61D 9/00; A61F 3/06; A61F 3/08
  USPC ........... 602/60, 61, 62, 63, 65, 41; 119/850; 54/82
  See application file for complete search history.

(56) References Cited

U.S. PATENT DOCUMENTS

| 4,926,851 A * | 5/1990 | Bulley ................. A61F 13/105 128/856 |
| 5,735,807 A * | 4/1998 | Cropper ................ A61F 5/0109 602/26 |
| 5,769,809 A * | 6/1998 | Witzel .................. A61F 2/7812 602/26 |
| 6,918,236 B2 | 7/2005 | Springs |
| 2004/0255955 A1 | 12/2004 | Daly |
| 2010/0106070 A1* | 4/2010 | Schlomski ........... A61F 5/0109 602/63 |
| 2010/0154366 A1* | 6/2010 | Petterson ............ A01K 13/007 54/82 |

* cited by examiner

*Primary Examiner* — Victoria J Hicks
(74) *Attorney, Agent, or Firm* — Renner, Otto, Boisselle & Sklar, LLP

(57) ABSTRACT

A breathable fabric sleeve provides varying elastic support to help heal strains, sprains and bruises to the ligaments and tendons of an animal's fetlock and pastern joints. Preferably the sleeve is made of a seamlessly woven elastic fabric. The sleeve is applied over the fetlock of the leg of a horse or other animal, from the pastern up to below the knee, on the front leg, or to below the hock, on the hind leg. The sleeve has uniform elastic strength around the circumference of the sleeve, but provides variable compression, so that an upper part of the sleeve provides greater circumferential compression and the lower part provides less compression. The variable compression can be produced by using a looser weave in a bottom end of the sleeve, and/or by increasing the diameter of the bottom end, relative to that of the central portion of the sleeve.

18 Claims, 4 Drawing Sheets

Fig. 1a
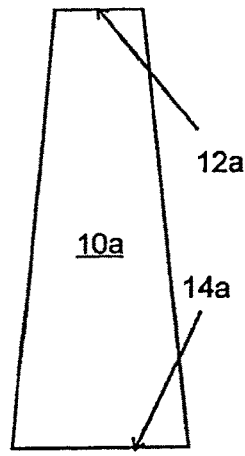
Fig. 1b
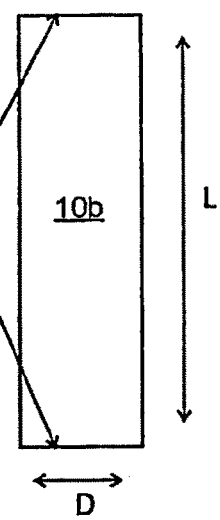
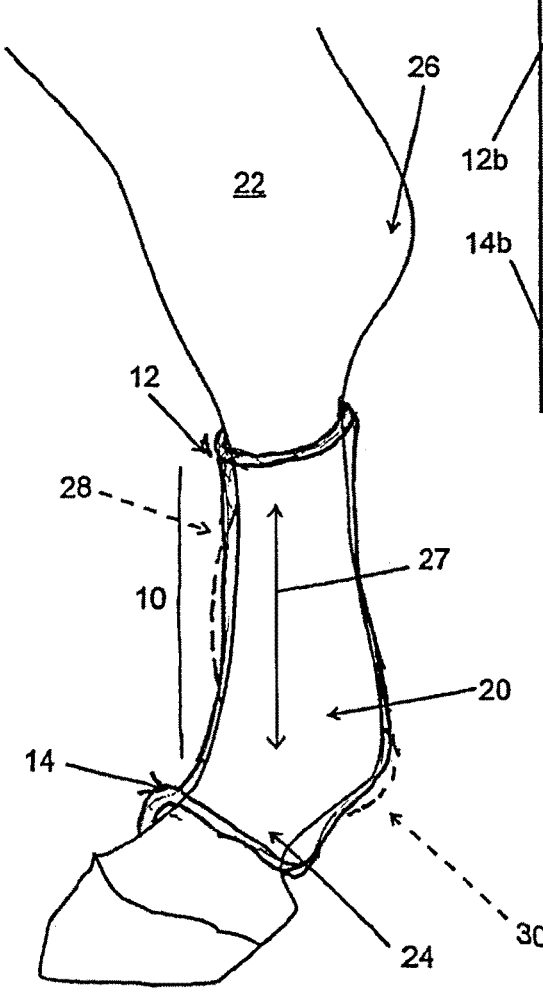
Fig. 1c

THERAPEUTIC JOINT SUPPORT FOR ANIMALS

This application claims the benefit of U.S. Provisional Application No. 61/395,809, filed May 18, 2010, which is incorporated herein by reference in its entirety.

BACKGROUND OF THE INVENTION

Field of the Invention

The invention relates to a support for the ligaments and tendons of a joint. More particularly, the present invention relates to a support for ligaments and tendons associated with the fetlock and pastern joints.

Description of the Related Art

Strains and sprains in a horse's lower leg that produce fluid retention and swelling have long been recognized in the horse industry as a hazard that causes not only temporary disability but also can cause consequential injuries and permanent disability, because horses are continually standing on the injured leg and distort their posture and gait to compensate for such injuries.

Therapeutic restraints, such as ankle boots and leg wraps, have been the standard devices used in veterinary practice for preventing further damage to strained, sprained and bruised legs when the animal stands on and moves that injured leg. However, both boots and traditional wraps have similar shortcomings, including causing abrasion, restricting joint motion, applying pressure at inappropriate points and trapping heat on the surface of the leg.

Although using boots during exercise, or during a turn-out to pasture, can maintain the integrity of an injured joint during exercise, conventional boots are too restrictive to be worn continually. For example, United States Patent Application No. 2004/0255955 (Daly) discloses a therapeutic boot that restricts joint motion during exercise. This may make exercise less risky but, once the boot is removed again in the barn, there is no support for that injured joint, which continues to bear the animal's weight. Without the boot's support, the injured joint then rapidly becomes inflamed and swollen.

Traditional leg wraps are made of quilted pads held tightly in place by elastic straps and reduce swelling by causing the horse's leg to sweat. However, once the swelling in that leg begins to dissipate, those pads and straps shift and slip as the horse moves. This shifting and slipping results in traditional leg wraps producing inappropriate pressure points during exercise and even in the barn. Those inappropriate pressure points produced by traditional leg wraps frequently irritate the horse's leg by catching the hair on the leg and abrading the skin on the horse's leg. Thus those inappropriate pressure points caused by the wraps that shift and slip as swelling decreases may further injure a horse's leg.

The inappropriate pressure points produced by traditional leg wraps may locally restrict circulation, which interferes with healing. In particular, when they slip they put pressure on the veins that pass in front of the horse's pastern joint and are important for controlling the swelling and inflammation that occur in the pastern and fetlock joints.

The occurrence of bowed tendons along the cannon bone has been attributed to excessive heat being retained by traditional leg wraps along the cannon bone. To lessen that heat buildup in the wrap, the leg wrap disclosed in U.S. Pat. No. 6,918,236 (Springs) provides a two-layer pad. Phase change microcapsules are embedded in a foam pad that is laminated to a breathable outer layer. However, because this wrap is still prone to slip and twist, it causes abrasion, interferes with circulation, and is not suitable for continuous wear as it may cause further injury.

SUMMARY OF THE INVENTION

The present invention provides a therapeutic joint support for leg strains, sprains and bruises, that reduces sweating, requires no additional padding, no belts, buckles or other adjustable devices, and resists slippage and shifting, so that it can be worn continuously and speeds healing.

In accordance with an embodiment, joint support is provided by an elastic sleeve having top and bottom hem, and a graduated elastic strength that decreases from the top hem to the bottom hem when the sleeve is applied to the circumferential surface of a cylinder having a constant diameter. The size and graduated elastic strength of the sleeve are selected for a given horse's leg so that the sleeve provides firm compression to the horse's fetlock, less compression along the cannon bone above the fetlock, and loosely encircles the pastern.

In one embodiment, the sleeve is made of a fabric that has a uniform elastic strength, but the sleeve has a substantially conical shape that is wider at the lower hem than at the upper hem.

In an alternative embodiment, the sleeve has a substantially cylindrical shape, but the elastic strength of the fabric is less at the lower hem than at the upper hem.

Preferably the sleeve is made of a breathable fabric so that sweating is reduced.

Preferably the sleeve is made of a smooth hosiery fabric that prevents chafing of the horse's hair and skin.

In one embodiment, the sleeve is seamlessly woven.

In another embodiment, the sleeve is seamlessly knitted.

According to yet another embodiment, an animal joint support includes an elastic sleeve that includes: a top end around a top opening; a bottom end around a bottom opening; and a central portion connecting the top end and the bottom end. The bottom end includes a reduced elastic strength region around the bottom opening, the reduced elastic strength region having a lower elastic strength than the central portion.

According to still another embodiment, a method of supporting an animal joint includes: providing an animal joint support, wherein the animal joint support includes an elastic sleeve that includes: a top end around a top opening; a bottom end around a bottom opening; and a central portion connecting the top end and the bottom end; and wherein the bottom end includes a reduced elastic strength region around the bottom opening, the reduced elastic strength region having a lower elastic strength than the central portion; and placing the animal joint support on a leg of an animal, wherein the placing includes placing the central portion over a fetlock of the animal leg, with the bottom end over a pastern joint of the animal leg.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

The annexed drawings, which are not necessarily to scale, illustrate aspects of the invention. In these drawings, similar structures have similar reference numbers.

FIG. 1a shows a hind leg joint support in accordance with the invention.

FIG. 1b shows an alternative to FIG. 1a in accordance with the invention.

FIG. 1c shows the sleeve of FIG. 1a or 1b applied to a horse's hind leg in accordance with the invention.

DETAILED DESCRIPTION

Figures 2A, 2B, 2C:
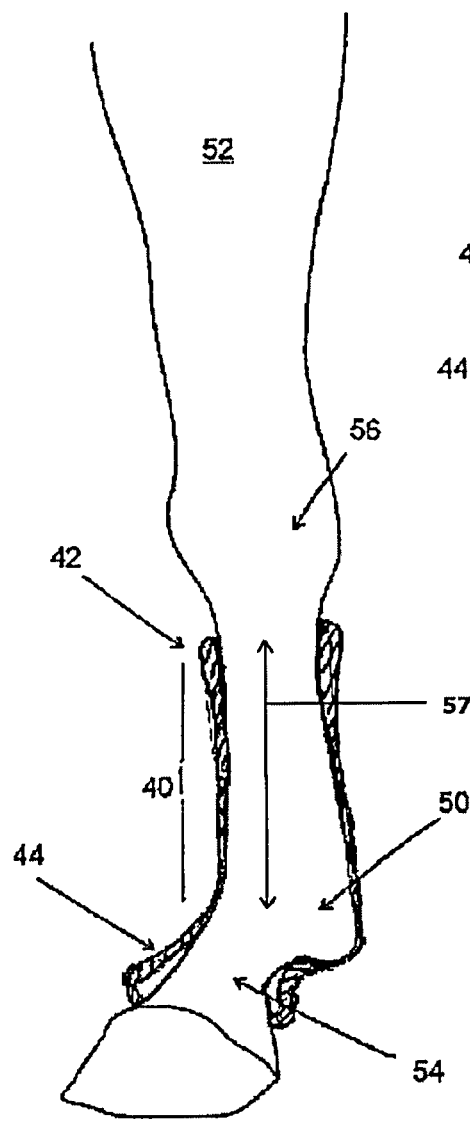
FIG. 2a shows a foreleg joint support in accordance with the invention.
FIG. 2b shows an alternative to FIG. 2a in accordance with the invention.
FIG. 2c is a cutaway view of the sleeve of FIG. 2a or 2b applied to a horse's foreleg in accordance with the invention.

A breathable fabric sleeve provides varying elastic support to help heal strains, sprains and bruises to the ligaments and tendons of an animal's fetlock and pastern joints. Preferably the sleeve is made of a seamlessly woven elastic fabric. The sleeve is applied over the fetlock of the leg of a horse or other animal, from the pastern up to below the knee, on the front leg, or to below the hock, on the hind leg. The sleeve has uniform elastic strength around the circumference of the sleeve, but provides variable compression, so that an upper part of the sleeve provides greater circumferential compression and the lower part provides less compression. The variable compression can be produced by using a looser weave in a bottom end of the sleeve, and/or by increasing the diameter of the bottom end, relative to that of the central portion of the sleeve. The length of the sleeve is selected so that, when the top hem is applied to the leg above the fetlock, the bottom hem of the sleeve loosely encircles the pastern, and elastic strength of the sleeve is selected so that the sleeve applies greater compression to the fetlock than to the leg above the fetlock.

FIG. 1a shows an embodiment of a joint support 10a for a horse's hind leg. The sleeve 10a is shaped as a truncated cone that flares slightly toward the lower end, and made of a durable, single-thickness breathable fabric. The sleeve is seamlessly woven so that the elastic strength of the fabric is constant around the circumference and constant from the top to the bottom of the sleeve 10a. The sleeve 10a has top and bottom hems 12a, 14a, that are smoothly woven into the fabric to finish these edges so as to prevent these edges from rubbing and fraying, without interfering with the flexibility of this fabric at its top and bottom edges 12a, 14a.

FIG. 1b shows an alternative possible embodiment of a joint support 10b for a horse's hind leg. The sleeve 10b is shaped as a constant-diameter tube that is also made of a durable, single-thickness breathable fabric. However, the elastic strength of the fabric in this sleeve 10b increases from the bottom edge 14b to the top 12b of the tube 10b. The sleeve 10a shown in FIG. 1a is preferable to this sleeve 10b because, when the elastic strength of the fabric is substantially constant, a sleeve size that will correctly fit a Shetland pony, or a Clydesdale, can be selected using the sleeve's length (L) from top to bottom and its diameter (D) at the top and bottom hems, 12a, 14a.

In FIG. 1c, a sleeve 10, such as one of the sleeves 10a, 10b, shown in FIGS. 1a and 1b, is pulled up over the horse's hoof and the fetlock joint 20 on a horse's hind leg 22. The length (L) is selected so that the sleeve 10 extends from the pastern joint 24 up to the minimum circumference of the hind leg 22 below the hock joint 26. The top and bottom diameters (D) of the sleeve 10 applied to the hind leg 22 are selected so that the bottom edge 14 loosely encircles the pastern joint 24, and so that the sleeve provides no more than a circumferential pressure of 70 mmHg to the leg 22. The size and graduated elastic strength of the sleeve 10 are selected so that the sleeve provides firm compression to the horse's fetlock 20, provides less compression along the cannon bone 27 below the hock 26 and above the fetlock 20, and loosely encircles the pastern joint 24 so that the sleeve 10 does not abrade or interfere with circulation in the front portion of the pastern 24. The outline of the horse's leg inside the sleeve 10 is shown to illustrate the firm compression provided over the fetlock joint 20, less compression along the cannon bone 27, and a loose fit around the pastern joint 24.

The profile 28 of an unsupported "bowed tendon" injury is shown in phantom in FIG. 1c. However this bowed tendon 28 is supported once the sleeve 10 is applied to the leg 22. Because the bottom edge 14 of the sleeve 10 loosely encircles the pastern joint 24, the sleeve 10 does not restrict circulation in the front portion of the pastern joint 24, and can also provide some support to a strained suspensory ligament 30 behind the pastern joint 24, without abrading or interfering with circulation in the front of the pastern joint 24.

FIG. 2a shows an embodiment of a joint support 40a for a horse's foreleg in accordance with the invention. Like the hind leg sleeve 10a, the foreleg sleeve 40a is also shaped as a truncated cone made of a durable, single-thickness breathable fabric. However, a foreleg sleeve 40a will usually be shorter and flare less toward the lower end than a hind leg sleeve 10a for a horse of the same size. Like the analogous hind leg sleeve 10a, the sleeve 40a is seamlessly woven so that the elastic strength of the fabric is constant around the circumference and constant from the top to the bottom of the sleeve 40a, and the sleeve 40a has top and bottom hems 42a, 44a, that are smoothly woven into the fabric without interfering with the flexibility of this fabric at its top and bottom edges 42a, 44a.

FIG. 2b shows an alternative possible embodiment of a joint support 40b for a horse's foreleg in accordance with the invention. Like the analogous hind leg sleeve 10 the foreleg sleeve 40b is shaped as a constant-diameter tube that is also made of a durable, single-thickness breathable fabric, and the elastic strength of the fabric in this sleeve 40b increases from the bottom edge 44b to the top 42b of the tube 40b. The foreleg sleeve 40a shown in FIG. 2a is also preferable to this foreleg sleeve 40b because it is easier to select the correct sleeve size when the elastic strength of the fabric is substantially constant.

Figure 2D:
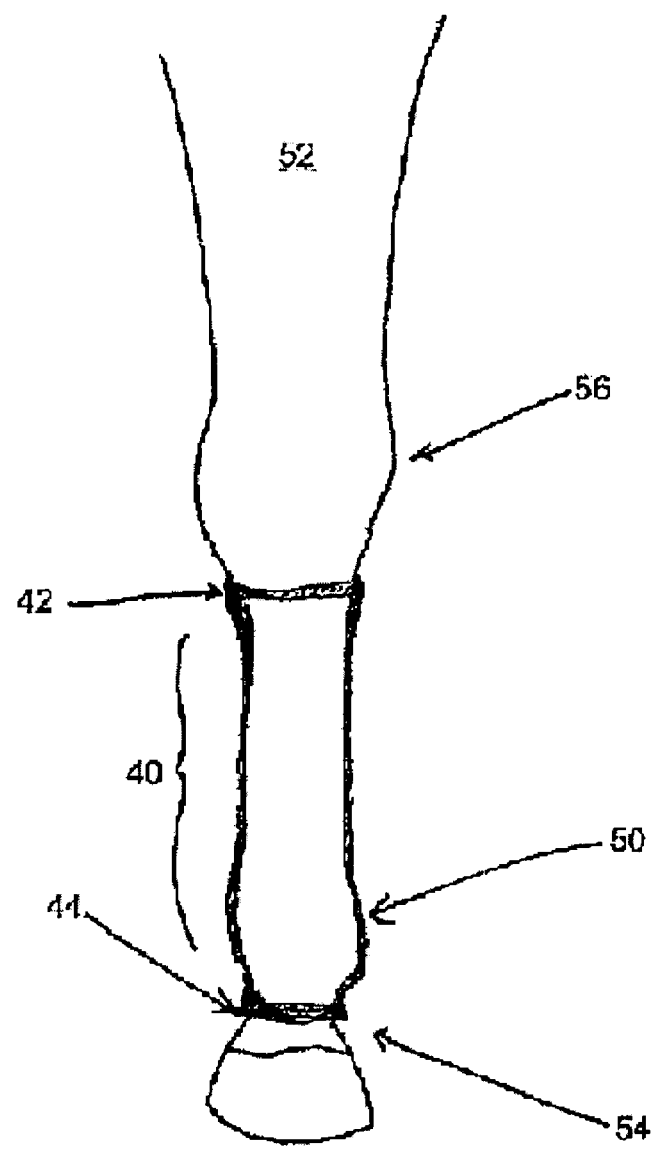
FIG. 2d is a front view of the foreleg and sleeve seen in side view in FIG. 2c, without the sleeve being cutaway.

In FIG. 2c, a sleeve 40, such as the sleeves 40a, 40b, shown in FIGS. 2a and 2b, is applied over the fetlock joint 50 of a horse's foreleg 52, and shown cutaway, to illustrate the loose fit around the pastern joint. Again, the length (L) is selected so that the sleeve 40 extends from the pastern joint 54 up to the minimum circumference of the foreleg 52 below the knee joint 56. Again the bottom edge 44 loosely encircles the pastern joint 54, so that the sleeve 40 provides a maximum circumferential pressure of 70 mmHg to the leg 52. Again, the size and graduated elastic strength of the sleeve 40 are selected so that the sleeve provides firm compression to the horse's fetlock 50, provides less compression along the cannon bone 57 above the fetlock 50, and loosely encircles the pastern joint 54 so that the sleeve 40 does not abrade or interfere with circulation in the front portion of the pastern 54. FIG. 2d provides a view of the front of the sleeve 40 that is seen in the cutaway side view shown in FIG. 2c.

The flexible support provided by these sleeves 10, 40, minimizes stiffness and soreness by supporting bruised, sprained or strained ligaments and tendons along the cannon bone 27, 57, and in the fetlock 20, 50 and pastern 24, 54 joints, and also by reducing consequential swelling and fluid accumulation in that part of the leg. Joint support that does not restrict leg motion and also minimizes swelling, stiffness and pain, makes exercise less likely to be impaired by the injury. In particular, increased comfort prevents the occurrence of the consequential back and hip injuries that occur when a horse distorts its gait to compensate for a sore leg. Also, because these flexible sleeves stimulate vascular function rather than acting as a restraint or interfering with circulation, the circulatory benefits of exercise are enhanced so that any joint swelling that occurs is further reduced, whether that swelling was caused by age, by injuries from improper exercise, or by accidental injury.

Because these breathable sleeves, unlike conventional leg wraps, reduce swelling without causing the sweating, they do not produce the inflammation and hair loss on an injured leg. Thus these compression sleeves 10, 40, provide greater comfort, than the restraints that are conventionally used for this purpose, and speed up the healing process.

The flexible support provided by the sleeve 10, 40, minimizes stiffness and soreness by supporting bruised, sprained or strained ligaments and tendons along the cannon bone 27, 57, and in the fetlock 20, 50 and pastern 24, 54 joints, and also by reducing consequential swelling and fluid accumulation in that part of the leg after exercise. The graduated elastic strength that these sleeves 10, 40 have, relative to a constant-diameter cylinder, also prevents the shifting and slippage of these sleeves 10, 40. The loose fit that this provides on the front of the pastern 24, 54 prevents abrasion, and avoids restricting circulation in that joint 24, 54, so that the sleeve can be worn continuously in ring and paddock, and in the barn. Furthermore, although as swelling decreases the sleeve 10, 40 will contract somewhat and continue to provide some pressure, thus resisting shifting and slippage, it can also be quite inexpensively replaced with a sleeve that provides firmer support, if desired.

Figure 3:
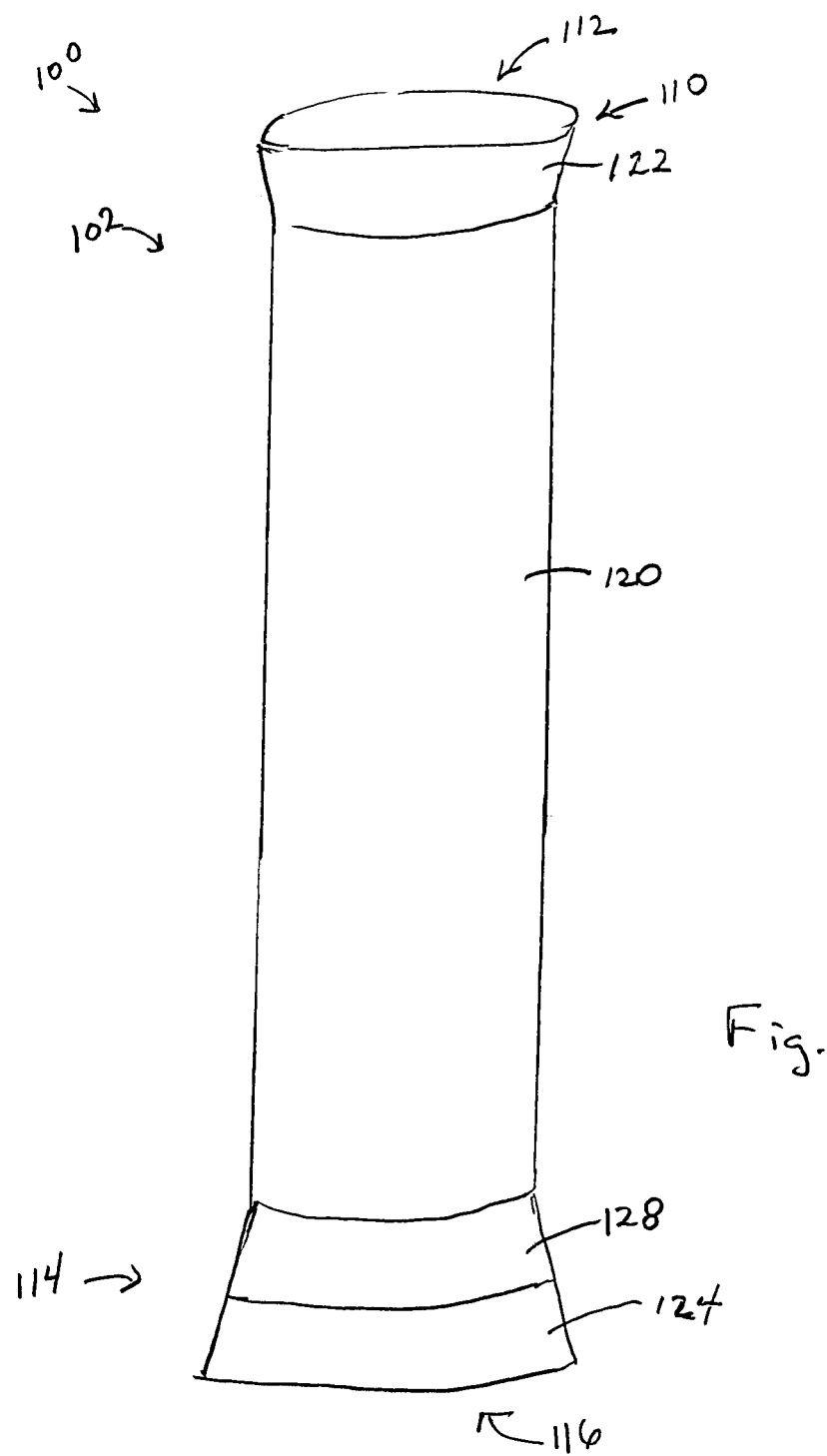
FIG. 3 is an oblique view of an animal joint support, in accordance with another embodiment.

FIG. 3 shows an animal joint support 100, an elastic sleeve 102 that fits around and supports a leg of an animal, such as a horse. The sleeve 102 may be made of a material (a yarn) that is a polyester-cotton blend, a material that is breathable. The sleeve 102 may be made of a single, seamless elastic piece. The sleeve 102 may be seamlessly woven or seamlessly knitted.

The sleeve 102 includes a top end 110 around a top opening 112, a bottom end 114 around a bottom opening 116, and a central portion 120 connecting the top end 110 and the bottom end 114. The top end 110 includes a folded-over top hem portion 122, and the bottom end 114 including a folded-over bottom hem portion 124. The bottom end 114 may also include a transition portion 128 that is between the central portion 120 and the bottom hem portion 124, connecting the portions 120 and 124 together. The central portion 120 and the transition portion 128 are single-layer portions, while the hem portions 122 and 124 are double-layer portions.

The central portion 120 may have a substantially-constant diameter over its length. The central portion 120 may have substantially-constant elastic strength, and therefore may provide a substantially-constant compression force over its length. The bottom end 114 includes a reduced elastic strength region around the bottom opening 116, a region which has a lower elastic strength than the central portion 120. In the illustrated embodiment the reduced elastic strength region is the entire bottom end 114, encompassing both the transition portion 128 and the bottom hem portion 124. However as an alternative the reduced elastic strength region may be only part of the bottom end 114. All or part of the top end 110 may also have an elastic strength that is less than that of the central portion 120. The top end 110 may also have an elastic strength that is greater than that of the reduced elastic strength region of the bottom end 114. The reduction of the elastic strength of all or part of the top end 110 and/or the bottom end 114 may be accomplished by a looser weave of the material than that in the central portion 120.

As used herein, "elastic strength" refers to the force opposing an elastic deformation of material. Thus a material with a relatively low elastic strength would provide less force opposing deformation than a material with a relatively high elastic strength.

Parts of the top end 110 and/or the bottom end 114 may have a greater diameter than that of central portion 120. For example the top end 110 and/or the bottom end 114 may flare out from the central portion 120. The (unstretched) diameter increase of the top end 110 and/or the bottom end 114 alternatively may be other than flaring, for example by a linear of increase of unstretched diameter as a function of distance from the central portion 120.

In one embodiment the sleeve 102 may have a length of 16 inches, with the central portion 120 having an unstretched diameter of 1.75 inches. The central portion 120 may account for a majority of the length of the sleeve 102, for example accounting for at least 75% of the length of the sleeve 102. The bottom end 114 may account for at least 10% of the length of the sleeve 102, for example accounting for at least 15% of the length of the sleeve 102. The top end 112 may account for about 10% of the length of the sleeve 102. A wide variety of other sizes for the sleeve 102 are possible, for instance to fit animals of different sizes.

In use, for the animal joint support 100 the central portion 120 provides compression over a fetlock of an animal, such as a horse. The top end 110 provides less compression along a cannon bone of the animal. The bottom end 114 loosely encircles a pastern joint of the animal. This provides relatively more compression on ligaments in the fetlock, while providing relatively less compression on a vascular area at a front of the pastern joint. In addition this may provide more compression on the cannon bone than on the pastern joint, and less compression on the cannon bone than on the fetlock.

In selecting a suitable joint support for use, an end user, such as a veterinarian, may make a selection from various joint supports of different sizes. There may be joint supports of different lengths, different diameters (e.g., the unstretched diameter of the central portion 120), different length/diameter combinations, different elastic strengths, and/or different combinations of these. The selection may be based at least in part on the size of the animal's leg, such as the length and/or diameter/circumference of the animal's leg. Another factor in the selection may be the animal's condition, with the type, placement, and/or severity of injury being a factor in selecting the appropriate joint support.

The joint supports described herein have the advantage of providing compression where needed to support an injured portion of animal, while not constricting bloodflow that will aid in healing of the injury. Joint supports of various sizes may be used to provide each injured animal with appropriate support to accomplish these objectives.

The joint supports have been described herein as for use for horses. Joint supports of similar configuration may be used with other sorts of animals. For example the joint supports may be used with other sorts of equine animals, such donkeys, burros, ponies, mules, and zebras. More broadly, such joint supports may be employed with other quadrapeds, such as dogs, for example.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. An animal joint support for a horse's leg comprising:
   an elastic sleeve including:
      a top end around a top opening;
      a bottom end around a bottom opening; and
      a central portion connecting the top end and the bottom end;
   wherein the bottom end includes a reduced elastic strength region around the bottom opening, the reduced elastic strength region having a lower elastic strength than the central portion;
   wherein the central portion has a constant diameter; and
   wherein the central portion has a length that is at least 75% of an overall length of the elastic sleeve.

2. The animal joint support of claim 1, wherein the bottom end increases diameter outward from the central portion.

3. The animal joint support of claim 2, wherein the top end increases diameter outward from the central portion.

4. The animal joint support of claim 1, wherein the bottom end has a looser weave than the central portion.

5. The animal joint support of claim 1, wherein the elastic sleeve is made of a breathable fabric.

6. The animal joint support of claim 1,
   wherein the bottom end increases diameter outward from the central portion;
   wherein the top end increases diameter outward from the central portion;
   wherein the elastic sleeve is a single, seamless elastic piece;
   wherein the elastic piece is a single-layer piece, with the central portion being a single-layer central portion, the top end including a folded-over top hem portion, and the bottom end including a folded-over bottom hem portion;
   wherein the bottom end also includes a single-layer transition portion, located between the central portion and the folded-over bottom hem portion;
   wherein the seamless elastic piece is seamlessly woven or seamlessly knitted; and
   wherein the elastic piece is made of a breathable fabric.

7. The animal joint support of claim 1, wherein the central portion has a substantially-constant elastic strength around a circumference of the central portion, over the length of the central portion.

8. The animal joint support of claim 1, wherein the central portion has a constant elastic strength around a circumference of the central portion, over the length of the central portion.

9. A method of supporting an animal joint, the method comprising:
   providing an animal joint support, wherein the animal joint support includes an elastic sleeve that includes:
      a top end around a top opening;
      a bottom end around a bottom opening; and
      a central portion connecting the top end and the bottom end; and
      wherein the bottom end includes a reduced elastic strength region around the bottom opening, the reduced elastic strength region having a lower elastic strength than the central portion; and
      wherein the bottom end increases diameter outward from the central portion; and
   placing the animal joint support on a leg of an animal,
   wherein the placing includes placing the central portion over a fetlock of the leg of the animal, with the bottom end over a pastern joint of the leg of the animal;
   wherein the placing provides relatively more compression on ligaments in the fetlock, while providing relatively less compression on a vascular area at a front of the pastern joint.

10. The method of claim 9, wherein the placing includes placing the top end over a cannon bone of the leg of the animal.

11. The method of claim 10, wherein the placing provides more compression on the cannon bone than on the pastern joint, and less compression on the cannon bone than on the fetlock.

12. The method of claim 9, wherein the placing results in the central portion being placed, without bunching, over the fetlock.

13. The method of claim 12, wherein the placing results in the bottom end loosely encircling the pastern joint.

14. The method of claim 9, wherein the providing includes selecting the animal joint support from multiple animal joint supports having different lengths, wherein the selecting is made based at least in part on size of the leg of the animal.

15. The method of claim 9, wherein the providing includes selecting the animal joint support from multiple animal joint supports having different central portion diameters, wherein the selecting is made based at least in part on size of the leg of the animal.

16. The method of claim 9, wherein the providing includes selecting the animal joint support from multiple animal joint supports having different combinations of length and central portion diameter, wherein the selecting is made based at least in part on size of the leg of the animal.

17. The method of claim 9, wherein the animal is a horse.

18. The method of claim 9,
wherein the central portion has a substantially constant diameter;
wherein the bottom end increases diameter outward from the central portion;
wherein the top end increases diameter outward from the central portion;
wherein the elastic sleeve is a single, seamless elastic piece;
wherein the elastic piece is a single-layer piece, with the central portion being a single-layer central portion, the top end including a folded-over top hem portion, and the bottom end including a folded-over bottom hem portion;
wherein the bottom end also includes a single-layer transition portion, located between the central portion and the folded-over bottom hem portion;
wherein the seamless elastic piece is seamlessly woven or seamlessly knitted; and
wherein the elastic piece is made of a breathable fabric.

* * * * *